United States Patent
Asai et al.

(10) Patent No.: US 10,398,134 B2
(45) Date of Patent: Sep. 3, 2019

(54) KNOCKOUT MOUSE, METHOD FOR SCREENING SUBSTANCE FOR SUPPRESSING MESIAL TEMPORAL LOBE EPILEPSY, AND METHOD FOR SELECTING TECHNIQUE FOR SUPPRESSING MESIAL TEMPORAL LOBE EPILEPSY

(71) Applicant: NATIONAL UNIVERSITY CORPORATION NAGOYA UNIVERSITY, Aichi (JP)

(72) Inventors: Masato Asai, Aichi (JP); Masahide Takahashi, Aichi (JP); Naoya Asai, Aichi (JP); Atsushi Enomoto, Aichi (JP); Kozo Uchiyama, Aichi (JP)

(73) Assignee: NATIONAL UNIVERSITY CORPORATION NAGOYA UNIVERSITY, Aichi (JP)

( * ) Notice: Subject to any disclaimer, the term of this patent is extended or adjusted under 35 U.S.C. 154(b) by 0 days.

(21) Appl. No.: 15/519,030

(22) PCT Filed: Oct. 13, 2015

(86) PCT No.: PCT/JP2015/078891
§ 371 (c)(1),
(2) Date: Apr. 13, 2017

(87) PCT Pub. No.: WO2016/060109
PCT Pub. Date: Apr. 21, 2016

(65) Prior Publication Data
US 2017/0223937 A1    Aug. 10, 2017

(30) Foreign Application Priority Data

Oct. 14, 2014 (JP) .................... 2014-210085

(51) Int. Cl.
| | |
|---|---|
| *A01K 67/027* | (2006.01) |
| *A01K 67/033* | (2006.01) |
| *G01N 33/50* | (2006.01) |
| *C12N 15/09* | (2006.01) |

(52) U.S. Cl.
CPC ........ *A01K 67/0276* (2013.01); *A01K 67/027* (2013.01); *G01N 33/5088* (2013.01); *A01K 2207/30* (2013.01); *A01K 2217/075* (2013.01); *A01K 2227/105* (2013.01); *A01K 2267/03* (2013.01); *A01K 2267/0356* (2013.01); *C12N 15/09* (2013.01); *G01N 2800/2857* (2013.01)

(58) Field of Classification Search
CPC .......... A01K 67/0276; A01K 2217/075; A01K 2227/105; A01K 2267/0356
USPC ..................................................... 800/9, 18
See application file for complete search history.

(56) References Cited

PUBLICATIONS

Carstea et al., 2009, World Journals of Stem Cells, vol. 1, No. 1, p. 22-29.*
Patil et al., 2011, Indian Journal of Public Health research & Development, vol. 2, No. 1, p. 106-109.*
Selsby et al., 2015, ILAR Journal, vol. 56, No. 1, p. 116-126.*
Nakai et al., 2012, Journal of Pharmacological Sciences, vol. 118, No. Suppl. 1, pp. 140P.*
Written Opinion of the International Searching Authority dated Jan. 12, 2016 issued in International Patent Application No. PCT/JP2015/078891 (with English translation).
M. Asai, et al., "Similar phenotypes of Girdin germ-line and conditional knockout mice indicate a crucial role for Girdin in the nestin lineage," Biochemical and Biophysical Research Communications, 2012, vol. 426, pp. 533-538.
T. Kitamura, et al., "Regulation of VEGF-mediated angiogenesis by the Akt/PKB substrate Girdin," Nature Cell Biology, 2008, vol. 10, No. 3, pp. 329-337.
K. Imaizumi, et al., "Epilepsy Like Anomaly of Mice," (Partial English translation) Department of Veterinary Science, Institute for Infectious Diseases, University of Tokyo, 1959, pp. 6-10.
S. Kogure, et al., "Platform Sessions," Epolepsia, vol. 38, Suppl. 6, 1997, pp. 58-83.
Ben-Ari "Kainate and temporal lobe epilepsies: Three decades of progress," Epilepsia, vol. 51, Suppl. 5, p. 40, 2010.
G. Curia, et al., "The pilocarpine model of temporal lobe epilepsy," J. Neurosci Methods, Jul. 30, 2008, vol. 172, pp. 143-157.
C. Craig, et al., "A Study of Pentylenetetrazol Kindling in Rats and Mice," Pharmacology Biochemistry & Behavior, (1989), vol. 31, pp. 867-870.
J. Delgado, et al., "Evolution of Repeated Hippocampal Seizures in the cat," Department of Physiology, Yale University School of Medicine, Neurophysiol, Mar. 27, 1961, pp. 722-733.
Sharma et al., "Mesial Temporal Lobe Epilepsy: Pathogenesis, Induced Rodent Models and Lesions" Toxicologic Pathology, 35:984-999 (2007).
Extended European Search Report issued in corresponding European Patent Application No. 15851535.3, dated Oct. 4, 2017.

* cited by examiner

*Primary Examiner* — Shin Lin Chen
(74) *Attorney, Agent, or Firm* — McDermott Will & Emery LLP

(57) ABSTRACT

Provided are a knockout mouse, a method for screening a substance for suppressing mesial temporal lobe epilepsy, and a method for selecting a technique for suppressing mesial temporal lobe epilepsy. A knockout mouse 30 or more days of age that has lost the function of the Girdin gene in at least the nervous tissues and exhibits the phenotypes of (1), (2), and (3) below. (1) hippocampal sclerosis should be present, (2) extrahippocampal brain damage should be limited, and (3) spontaneous epilepsy that can be said to be of hippocampal origin should be present.

3 Claims, 13 Drawing Sheets

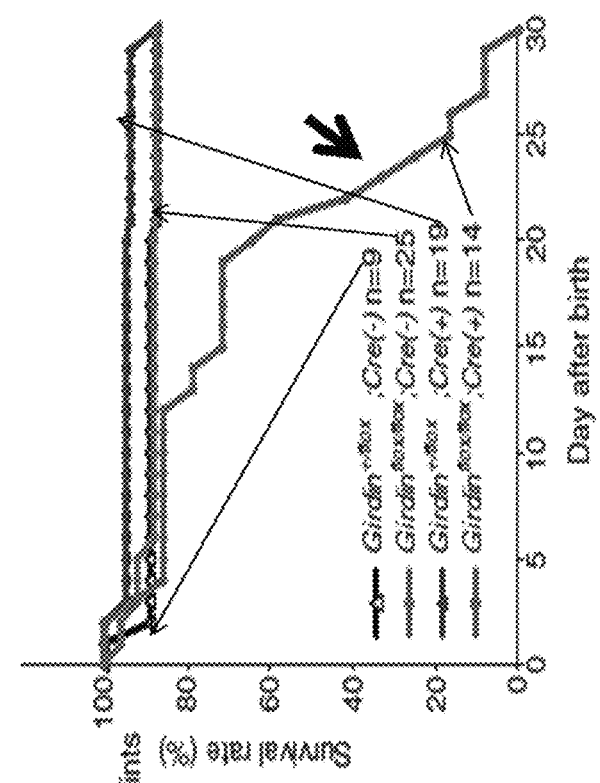
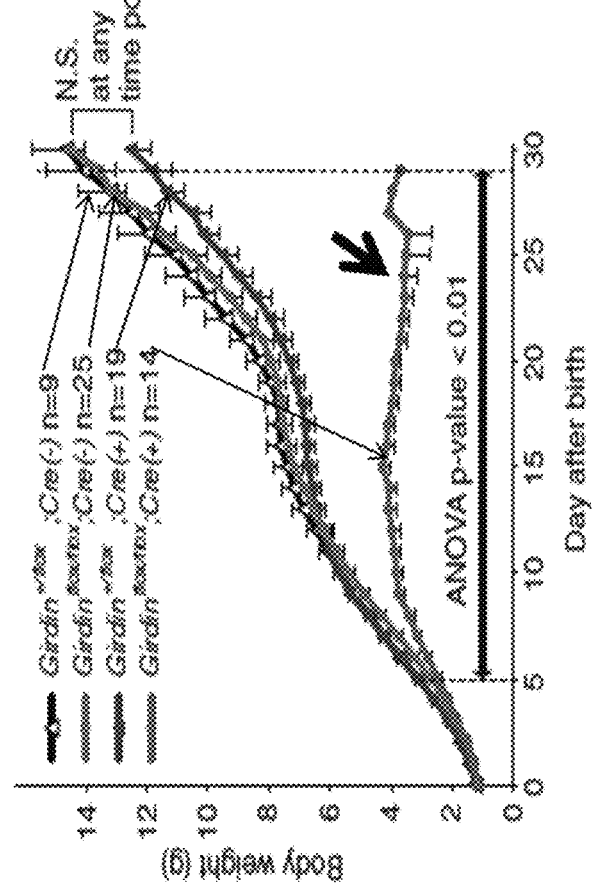
FIG. 2A
FIG. 2B

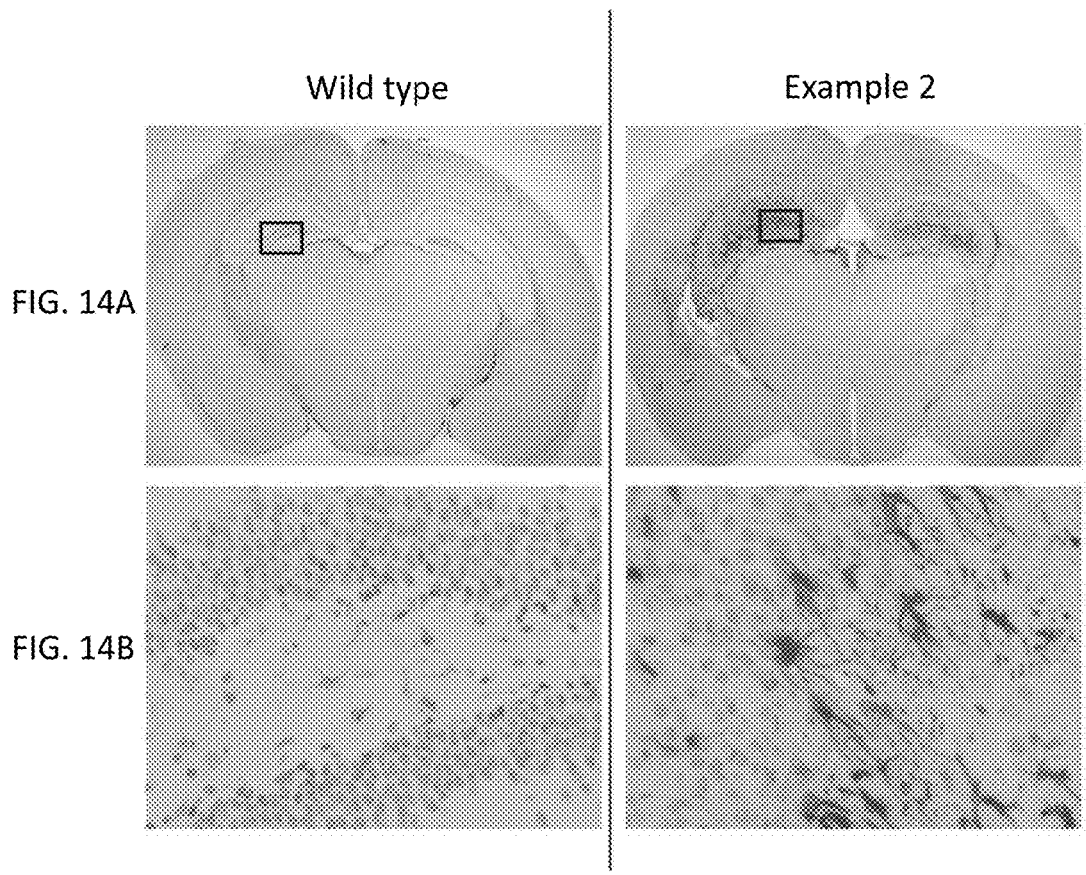
FIG. 14A
FIG. 14B
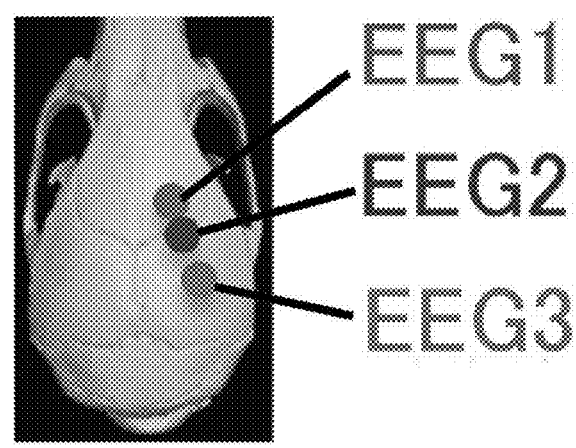
FIG. 15

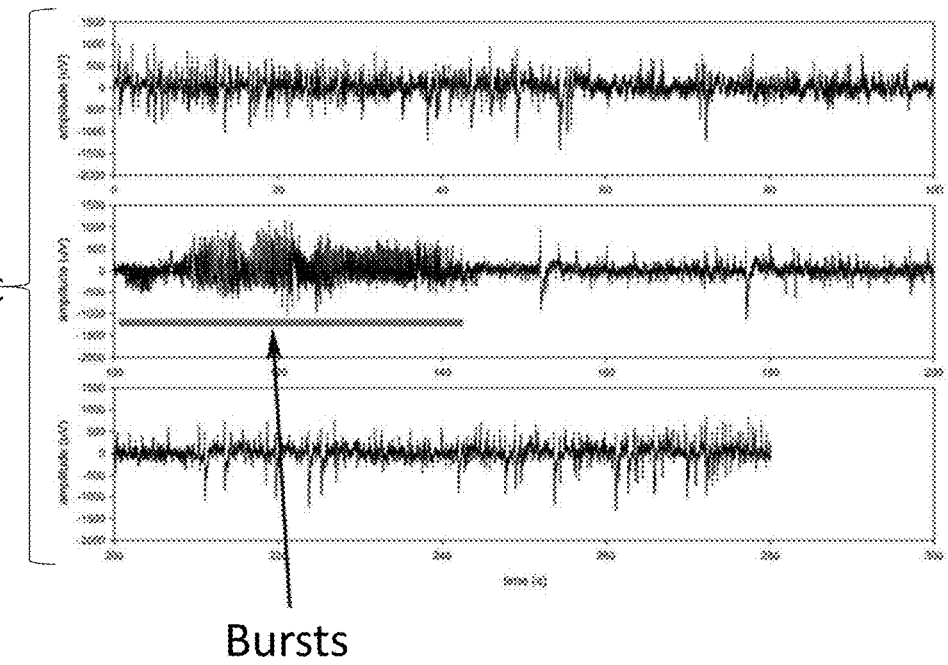
Bursts

KNOCKOUT MOUSE, METHOD FOR SCREENING SUBSTANCE FOR SUPPRESSING MESIAL TEMPORAL LOBE EPILEPSY, AND METHOD FOR SELECTING TECHNIQUE FOR SUPPRESSING MESIAL TEMPORAL LOBE EPILEPSY

CROSS-REFERENCE TO RELATED APPLICATIONS

This application is the U.S. National Phase under 35 U.S.C. § 371 of International Patent Application No. PCT/JP2015/078891, filed on Oct. 13, 2015, which in turn claims the benefit of Japanese Application No. 2014-210085, filed on Oct. 14, 2014, the disclosures of which Applications are incorporated by reference herein.

FIELD OF THE INVENTION

The present invention relates to a knockout mouse, a method for screening a substance for suppressing mesial temporal lobe epilepsy, and a method for selecting a technique for suppressing mesial temporal lobe epilepsy.

DESCRIPTION OF THE RELATED ART

Mesial temporal lobe epilepsy (sometimes referred to hereinafter as "MTLE") is a representative drug therapy-resistant epilepsy in adults. The seizure focus is the hippocampal dentate gyrus. It is a serious disease related not only to so-called epileptic seizures (tonic-clonic seizures—grand mal seizures) associated with loss of consciousness and falls, but also to runaway accidents if automatism that allows acting in a dream state occurs in a vehicle driver.

During the interictal interval, MTLE patients are hypersensitive to all of the senses (sight, touch, sound, taste, and smell) as expressed by the distinctive "syndrome of sensory-limbic hyperconnection" (D M Bear, 1979) and exhibit an impulsive personality disorder. The root cause of the onset of MTLE is not well understood, and there is currently no effective treatment other than amygdalohippocampectomy. The identification of drug therapy targets is therefore required, and animal models that accurately imitate human MTLE are needed to identify drug therapy targets, screen therapeutic drugs, and select therapeutic techniques.

The conditions required of an MTLE animal model in the authoritative book *Progress in Epileptic Disorders*, "The Mesial Temporal Lobe Epilepsies," edited by Felix Rosenow, Philippe Ryvlin, and Hans Luders, published by John Libbey Eurotext, are (1) hippocampal sclerosis should be present,
(2) extrahippocampal brain damage should be limited, and
(3) spontaneous epilepsy regarded to be of hippocampal origin should be present.

Spontaneous epilepsy models such as the EL mouse (see Nonpatent Document 1) and Ihara's rat (see Nonpatent Document 2) and model mice inducible using kainic acid (see Nonpatent Document 3), pilocarpine (see Nonpatent Document 4), PTZ (see Nonpatent Document 5), and electroshock (see Nonpatent Document 6) are known as MTLE animal models. However, a problem is presented in that which mice will become epileptic in the future cannot be predicted at the time of birth because the causative gene is not known in the spontaneous models, and the drug and electroshock dosages are difficult to adjust in mice inducible by drugs and electroshock. Another drawback is that induction causes extensive damage to areas other than the hippocampal dentate gyrus. Other problems are that the number of attacks cannot be anticipated in advance and there is no guarantee that the attacks originate from the hippocampus. Mice that fulfill the conditions required by Felix Rosenow et al. are not currently known.

Therapeutic drugs (therapeutic methods) required in the treatment of epilepsy patients, including MTLE, should eliminate or decrease "automatism" and "grand mal seizures". A "grand mal seizure" is easier to define objectively than "automatism," which is difficult to define and to determine whether consciousness is present, and the number of seizures can be counted because the beginning and end are clear. The EEG and video observation are the two main techniques for observing grand mal seizures. EEG measurement in mice requires expert technique to open the scalp of the mouse and pierce the skull with electrodes and expensive measurement and analysis systems. In contrast to this, determination of grand mal seizures by video filming does not require expert technique, can be done relatively simply, and can clearly confirm the existence of an effect of a therapeutic drug or technique. The problem with all methods, however, is that the existence of an effect of a therapeutic drug or technique cannot be observed over an extended period of time since mice that fulfill the conditions required by Felix Rosenow et al. are not known.

A protein called the actin-binding protein Girdin (girders of actin filament) is known. This protein is known to be expressed strongly in vivo in immature vascular endothelial cells, hippocampal neurons, and neurons constituting the subventricular zone and rostral migratory stream (RMS) important for olfactory bulb formation. It is also known as a result of producing Girdin knockout mice and analyzing its role within the body that vascular networks of the retina and cerebrum formed after birth and structural abnormalities of the hippocampus and olfactory bulb are found histologically even though there are no clear macroscopic changes in the knockout mice immediately after birth in comparison to the wild type (see Nonpatent Document 7).

In the Girdin knockout mice described in Nonpatent Document 7, Girdin knockout mice are produced by inserting a lacZ into exon 2 of the Girdin gene. The present inventors, however, succeeded in producing Girdin knockout mice by mating transgenic mice having exon 3 of the Girdin gene flanked by a loxP sequence (flox) and recombinant protein Cre driven by a nestin promoter (Nonpatent Document 8). With the Girdin knockout mice described in Nonpatent Document 7, the wild type is born at a probability of 1/4, hetero type at a probability of 1/2, and homo type Girdin knockout mice at a probability of 1/4 according to Mendel's law from heterozygous parents as described below. With the Girdin knockout mice described in Nonpatent Document 8 as well, knockout mice that are Cre positive and homo flox type are born at a probability of 1/4 by mating a Cre-positive hetero flox type parent and a Cre-negative homo flox type parent.

PRIOR ART DOCUMENTS

Nonpatent Documents

[Nonpatent Document 1] Kiyoshi Imaizumi, Shogo Ito, Genshiro Kutsukake, Takayasu Takizawa, Kiminari Fujiwara, Kiyoshi Tsuchikawa, "Epilepsy-like anomaly of mice," April 1958, Jikken Dobutsu [Experimental Animals] 8(1): p. 6-10

[Nonpatent Document 2] Amano S et.al "Microdysgenesis in the Hippocampal Formation of Ihara's Genetically Epileptic Rats (IGER):Comparative Study of IGER and its Original Strain ICR and Substrain IGER/c(-)", Epilepsia, 1997 Vol. 38 supplement p61

[Nonpatent Document 3] Ben-Ari, Y. "Kainate and Temporal Lobe Epilepsies: Three decades of progress", Epilepsia, 2010 51(Suppl. 5), p40

[Nonpatent Document 4] Curia G, Longo D, Biagini G, Jones R S, Avoli M. "The pilocarpine model of temporal lobe epilepsy." Journal of Neuroscience Methods 2008 Jul. 30, Vol. 172(2-4):p143-57

[Nonpatent Document 5] Charles R. Craig et.al "A Study of Pentylenetetrazol Kindling in Rats and Mice" Pharmacology Biochemistry & Behavior,1989, Vol. 31, p867-70

[Nonpatent Document 6] Jose M. R. Delgado, Manuel Sevillano, "Evolution of repeated hippocampal seizures in the cat" Electroencephalography and clinical neurophysiology., 1961, Vol. 13, p722-33

[Nonpatent Document 7] Kitamura. T et al., "Regulation of VEGF-mediated angiogenesis by the Akt/PKB substrate Girdin", Nature Cell Biology, Vol. 10, No. 3, March 2008, p329-337 & SUPPLEMENTARY INFORMATION, p1-7

[Nonpatent Document 8] Asai M et al., "Similar phenotypes of Girdin germ-line and conditional knockout mice indicate a crucial role for Girdin in the nestin lineage", Biochemical and Biophysical Research Communications, 2012 Oct. 5; Vol. 426(4):p533-8

SUMMARY OF THE INVENTION

Problems to be Solved by the Invention

As described above, Girdin knockout mice are already known. However, a problem is presented in that these Girdin knockout mice all die in infancy, and adults cannot be obtained.

FIGS. 1A and 1B are graphs described in FIG. S5.C of Nonpatent Document 7. FIG. 1A shows the weight curves of the wild type (n=14), hetero type (n=32), and homo type (Girdin knockout mouse, n=17). FIG. 1B shows the survival rates. As is evident from FIGS. 1A and 1B, the growth of the homo type begins to slow in comparison to that of their wild type and hetero type littermates from day eight after birth. In addition, all of the homo type died by day 25 after birth in contrast to survival of basically 100% of the wild type and about 90% of the hetero type littermates approximately 30 days after birth, which is the time of weaning.

FIGS. 2A and 2B are graphs described in FIG. 4 of Nonpatent Document 8. FIG. 2A shows the weight curves; FIG. 2B shows the survival rates. As is evident from FIGS. 2A and 2B, the growth of the Girdin knockout mice (n=14) shown by ↓ begins to slow in comparison to that of the other littermates (n=53) from five days after birth. In addition, all of the Girdin knockout mice died by day 29 after birth in contrast to survival of about 90% of the other littermates approximately 30 days after birth, which is the time of weaning.

Therefore, although Girdin knockout mice themselves are known, a problem is presented in that all die before becoming adults, making them difficult to apply in experiments using this knockout mouse.

The present invention is an invention intended to solve the above problems of the prior art. As a result of in-depth research, it was clarified that (1) Girdin knockout adult mice are obtained by changing the method of feeding the mice, (2) MTLE develops during the course of observing the adult mice, and it was also newly discovered as a result of analysis of the brain tissue of the mice that Girdin knockout mice fulfill the above conditions required of an MTLE animal model, (3) that obtaining Girdin knockout adult mice makes it possible to screen substances for suppressing MTLE and to select techniques for suppressing MTLE, and (4) that substances for suppressing MTLE can be screened over an extended period of time and techniques for suppressing MTLE can be selected over an extended period of time by video observation without requiring expert technique since the Girdin knockout mice obtained by the present invention survive for a long time.

Specifically, the purpose of the present invention is to provide a knockout mouse, a method for screening a substance for suppressing mesial temporal lobe epilepsy, and a method for selecting a technique for suppressing mesial temporal lobe epilepsy.

Means for Solving the Abovementioned Problems

The present invention relates to a knockout mouse, a method for screening a substance for suppressing mesial temporal lobe epilepsy, and a method for selecting a technique for suppressing mesial temporal lobe epilepsy shown below.

[1] A knockout mouse 30 or more days of age that has lost the function of the Girdin gene in at least the nervous tissues and exhibits the phenotypes of (1), (2), and (3) below.

(1) hippocampal sclerosis should be present, (2) extrahippocampal brain damage should be limited, and (3) spontaneous epilepsy that can be said to be of hippocampal origin should be present.

[2] A knockout mouse 30 or more days of age that has lost the function of the Girdin gene in at least the nervous tissues.

[3] The knockout mouse according to [1] or [2] above, wherein the knockout mouse is raised on soft feed.

[4] The knockout mouse according to [3] above, wherein the soft feed is jelly-like.

[5] A method for screening a substance for suppressing mesial temporal lobe epilepsy including, a step for administering a candidate substance to the knockout mouse according to any one of [1] to [3] above, a step for selecting a substance that suppresses mesial temporal lobe epilepsy.

[6] A method for screening a substance for suppressing mesial temporal lobe epilepsy including, a step for administering a candidate substance to the knockout mouse according to [4] above, a step for selecting a substance that suppresses mesial temporal lobe epilepsy.

[7] A method for selecting a technique for suppressing mesial temporal lobe epilepsy including, a step for performing a technique for suppressing mesial temporal lobe epilepsy on the knockout mouse according to any one of [1] to [3] above, a step for selecting a technique for suppressing mesial temporal lobe epilepsy.

[8] A method for selecting a technique for suppressing mesial temporal lobe epilepsy including, a step for performing a technique for suppressing mesial temporal lobe epilepsy on the knockout mouse according to [4] above, a step for selecting a technique for suppressing mesial temporal lobe epilepsy.

[9] The method for screening a substance for suppressing mesial temporal lobe epilepsy according to [5] or [6] above, wherein the step for selecting a substance for suppressing mesial temporal lobe epilepsy conducts video observation of knockout mice and selects a substance by suppressing the frequency and/or severity of seizures.

[10] The method for selecting a technique for suppressing mesial temporal lobe epilepsy according to [7] or [8] above, wherein the step for selecting a technique for suppressing mesial temporal lobe epilepsy conducts video observation of knockout mice and selects a technique by suppressing the frequency and/or severity of seizures.

Conventional Girdin knockout mice could only survive up to 29 days after birth, which is infancy, but the Girdin knockout mice of the present invention can be raised for one year or more as adults. Therefore, they can be used in various experiments that utilize Girdin knockout mice.

A drawback of conventional mice induced by drugs and electroshock has been extensive damage to other than the hippocampus that serves as the cause of MTLE. The Girdin knockout mice of the present invention, however, fulfill the conditions required of an MTLE animal model. The Girdin knockout mice therefore can be used in screening of substances for suppressing MTLE and selection of techniques for suppressing MTLE.

Since the Girdin knockout mice of the present invention develop epilepsy due to loss of the function of the Girdin gene, the epileptogenic mechanism of the mice produced is the same. Therefore, since individual differences between the Girdin knockout mice produced exert virtually no effect, it is possible to efficiently screen substances for suppressing epilepsy and select techniques for suppressing epilepsy.

The Girdin knockout mice of the present invention survive a long time and therefore make it possible to screen substances for suppressing MTLE and observe the selection efficacy of techniques for suppressing MTLE.

Since the Girdin knockout mice of the present invention survive for a long time, it is possible to screen substances for suppressing MTLE and select techniques for suppressing MTLE by video observation, and commercial video equipment can be used without the expert technique required for EEG measurement or the use of expensive measurement and analysis systems. Video observation, in comparison to the EEG, also makes it possible to clearly distinguish and observe sleep, feeding, and other behaviors.

BRIEF DESCRIPTION OF THE DRAWINGS

FIG. 1A shows the weight curves of the wild type (○m wild type, n=14), hetero type (■, Girdin +/−, n=32), and homo type (♦, Girdin −/−, Girdin knockout mice, n=17). FIG. 1B shows the survival rates.

FIGS. 2A and 2B are described in FIG. 4 of Nonpatent Document 8. In FIG. 2A, ↓ shows the weight curve of Cre-positive and homo flox type, that is, Girdin knockout mice, and Δ, ●, ▲ show mice of other karyotypes. FIG. 2B shows the survival rates of mice of each karyotype by the same symbols as in FIG. 2A.

FIG. 5A is a photograph showing the feeding method before switching the feed, and FIG. 5B is a photograph showing the feeding method after switching the feed.

FIG. 13A is photographs of sagittal paraffin sections of the brains of Example 1 and wild type mice that have been immunostained using GFAP antibody and nuclear stained by hematoxylin. FIG. 13B is enlarged photographs of the parts surrounded by square of FIG. 13A.

FIGS. 14A and 14B are photographs substituted for a drawing. FIG. 14A is photographs of coronal paraffin sections of the brains of Example 2 and wild type mice that have been immunostained using GFAP antibody and nuclear stained by hematoxylin. FIG. 14B is enlarged photographs of the parts surrounded by square of FIG. 14A.

FIG. 15 shows the positions of the electrodes (EEG1, EEG2, EEG3) embedded in the skull of a mouse.

FIG. 16C shows the EEG of a mouse of Example 2 during a grand mal seizure.

DESCRIPTION OF THE PREFERRED EMBODIMENTS

Figures 1A, 1B:
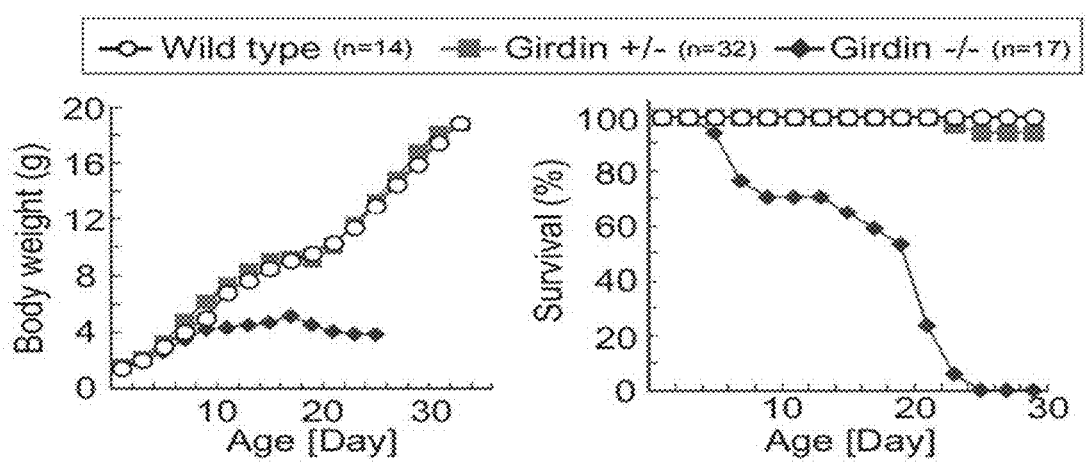
FIGS. 1A and 1B are described in FIG. S5.C of Nonpatent Document 7.

The knockout mouse, method for screening a substance for suppressing mesial temporal lobe epilepsy, and method for selecting a technique for suppressing mesial temporal lobe epilepsy of the present invention are explained in detail below.

First, among the conditions required of an MTLE animal of the present invention, (1) "hippocampal sclerosis should be present" is a representative lesion of MTLE and means that neuronal loss and hyperplasia of activated astrocytes are found in the hippocampal ammonic horn, especially the pyramidal cell layer of the CA1 region, and the granule cell layer of the hippocampal dentate gyrus.

(2) "extrahippocampal brain damage should be limited" means that there is no sclerosis characterized by activated astrocytes in other than the hippocampus in staining by GFAP antibody, or if there is extrahippocampal sclerosis, it is in locations adjacent to the hippocampus such as the amygdala or parietal cerebral cortex.

(3) "spontaneous epilepsy that can be said to be of hippocampal origin should be present" means that epileptic seizures occur without pharmacological or physical induction by drugs or electroshock.

In the present invention, "a substance for suppressing mesial temporal lobe epilepsy" and "a technique for suppressing mesial temporal lobe epilepsy" mean substances and techniques that not only completely suppress the onset of MTLE but also that alleviate the frequency of epileptic seizures and/or symptoms of epilepsy on various levels. Examples of substances for suppressing MTLE include natural compounds, organic compounds, inorganic compounds, proteins, antibodies, peptides, and other such single compounds as well as compound libraries, expression products of gene libraries, cell extracts, cell culture supernatants, fermented microbial products, marine organism extracts, plant extracts, and the like. These substances are not particularly restricted as long as they are taken into the body of the knockout mouse by oral administration, adhesion to the skin, administration to the body by injection, or the like.

Examples of techniques for suppressing MTLE include epileptic seizure therapies such as vagus nerve stimulation (VNS), massage, orthosis, and treatments relating to lifestyle (diet, type of diet, exercise, etc.). Substances or techniques for suppressing MTLE may each be screened and combinations of substances and techniques may be screened using the Girdin knockout mice of the present invention.

The Girdin gene information, cDNA sequences, and amino acid sequences of mice and humans are known. For example, the gene information of GenBank Gene ID: CCDC88A, cDNA described in GenBank accession no. NM_176841, and amino acid sequence information described in GenBank accession no. Q5SNZO can be obtained for mice. The gene information of GenBank Gene ID: CCDC88A, cDNA described in GenBank accession no. NM_018084.4, and amino acid sequence information described in GenBank accession no. Q3V6T2 can be obtained for humans.

Knockout mice that have lost the function of the Girdin gene may be produced by a known method, for example, by the following procedure.

(a) The gene to be knocked out is separated from the genome of the mouse. Then, a base sequence including the gene and its surrounding parts is created; it is not exactly the same, but partially modified so as to inactivate it. Partial modification is generally carried out by incorporating marker genes that cause an observable difference (color, fluorescence, etc.).

(b) Embryonic stem cells from a mouse blastocyst (early mouse embryo, spherical undifferentiated cells surrounded by extraembryonic cells) are separated. The embryonic stem cells can be cell cultured in vitro, for example, using embryonic stem cells of gray mice.

(c) The base sequence produced in (a) above is introduced into the embryonic stem cells obtained in (b) above using a means such as electroporation. Next, the marker genes incorporated in (a) above are utilized, and embryonic stem cells (heterozygous) in which recombination to the new base sequence has actually occurred are separated.

(d) The embryonic stem cells that have undergone homologous recombination separated in (c) above are, for example, injected into the blastocyst of a black mouse, this blastocyst is injected into the uterus of a female mouse, and a child mouse is born. This child mouse becomes a chimera including two lines of cells, with part of the body derived from the original blastocyst and other parts derived from the genetically engineered embryonic stem cells. Its fur color therefore becomes mottled black and gray.

(e) Only those of the chimeric mice in which the germ cells (ova or sperm) derive from the genetically engineered cells are utilized. These mice are crossed with black mice to obtain children mouse (usually called F1). The F1 mice still have one or more functional genes (heterozygous), but mice that do not have the original functional gene (that is, homozygotic) are created by inbreeding.

Figure 3:
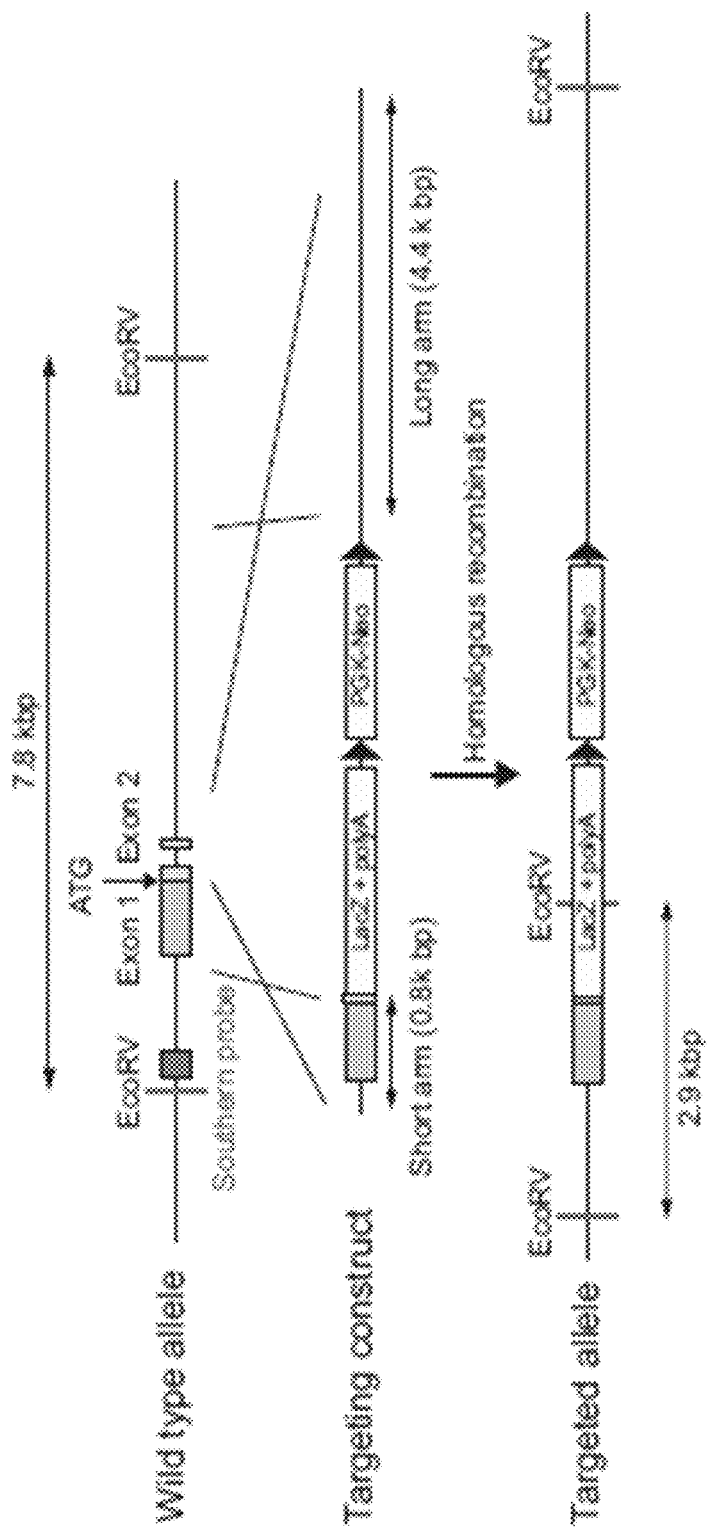
FIG. 3 shows a gene modification diagram of a Girdin knockout mouse described in Nonpatent Document 7.
Figure 4:
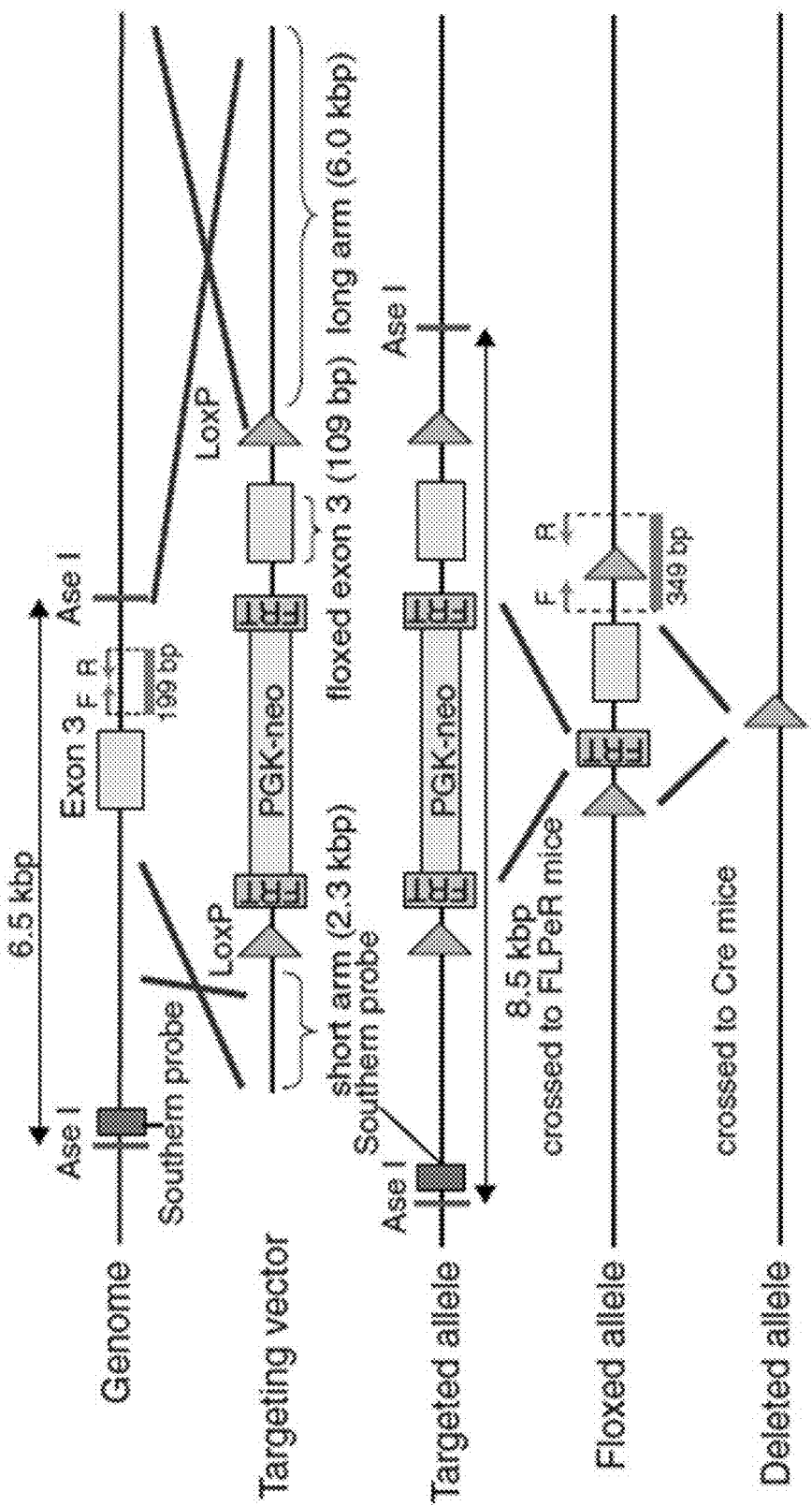
FIG. 4 shows a gene modification diagram of a Girdin knockout mouse described in Nonpatent Document 8.

FIG. 3 shows a gene modification diagram of a Girdin knockout mouse described in Nonpatent Document 7. FIG. 4 shows a gene modification diagram of a Girdin knockout mouse described in Nonpatent Document 8. The Girdin gene is constructed of 33 exons. By modifying an exon on the upstream side of the gene, the amino acid sequence and stop codon position are changed by shifting the reading frame of the gene on the downstream side of that exon, and the Girdin function of the mouse produced can be extinguished. Furthermore, the gene modification diagrams shown in FIGS. 3 and 4 are simply examples, and other parts of the Girdin gene may be modified, for example, modification of exon 4 or exon 5, knocking of a lacZ gene or neomycin resistance gene, or other such marker gene, as long as the function of Girdin has been extinguished from the mouse produced.

A method for feeding the mice is devised in the present invention. As described in Nonpatent Documents 7 and 8, conventional Girdin knockout mice could only be raised for a maximum of 29 days. Instead of the conventional method of placing solid feed in a frame on the rearing cage ceiling, the present inventors use soft feed and a method of placing the soft feed inside the rearing cage. In the present invention, "soft feed" means feed that contains nutrients and moisture, for example, watery feed that contains nutrients, feed obtained by making a jelly by adding agar or the like to this watery feed that contains nutrients, jelly-like feed obtained by compacting a known powdered feed for mice with water and agar, soaked feed obtained by adding water to the powdered feed, and the like. These feeds may be used individually or in combination. The location where the feed is placed should be a location within the rearing cage where the mice can eat the feed easily. For example, a dish containing the feed may be placed on the shavings in the rearing cage or on a side wall of the cage, or the like. Furthermore, the mice may spill it when a watery feed is placed on the shavings. It is therefore preferable to use jelly-like feed or feed obtained by soaking powdered feed in water from the viewpoint of rearing convenience as well as the viewpoint of the ease of handling the feed by the person doing the feeding.

Although it is not clear why adult Girdin knockout mice are obtained by the above method, factors are presumed to include:

(1) since the feed is placed within the rearing cage, stress is reduced on the mother mouse raising the young that are nursing and eating by taking feed from a frame on the rearing cage ceiling, (2) because soft feed is placed within the rearing cage, the young mice can make a stress-free transition from weaning from the mother mouse to eating feed, and the like.

In screening a substance for suppressing MTLE, the Girdin knockout mice produced may be placed in a rearing cage, given soft feed containing a candidate substance or administered a candidate substance separately from the feed by injection or the like, and observed by video. Furthermore, a known video observation system may be used as the video observation system, but it is preferable to use an observation system that permits night vision to allow 24-hour continuous observation over many days.

In screening a technique for suppressing MTLE, the Girdin knockout mice produced may be placed in a rearing cage, subjected to an epileptic seizure treatment such as vagus nerve stimulation (VNS), subjected to massage, fitted with a corset or a soundwave or vibration stimulation generator, subjected to therapy related to lifestyle (adjustment of diet and/or type of diet, exercise, etc.), observed by video in the same way as above, and the effects of the technique observed. When used in combination with screening a substance, the technique may be screened while administering a candidate substance. Furthermore, 24-hour continuous observation can be performed when video observation is used as described above as a method for screening a substance for suppressing MTLE and a method for selecting a technique for suppressing MTLE, but methods are not limited to video observation. Since 100% of the Girdin knockout mice of the present invention develop MTLE, substances for suppressing MTLE may be screened and techniques for suppressing MTLE may be selected by methods such as histopathological observation, brain RNA extraction and analysis, measurement of motor activity by infrared beam, and the like after administration of a candidate substance and/or performance of a technique for suppressing MTLE.

The present invention is explained concretely below through examples. The examples, however, are merely provided as a reference for specific embodiments to explain the present invention. These examples are intended to explain specific embodiments of the present invention, but in no way limit or restrict the scope of the invention disclosed in this specification.

EXAMPLES

Example 1

[Production of Girdin Knockout Mice]
Girdin knockout mice were produced according to the procedure described in Nonpatent Reference 7.

Example 2

Girdin knockout mice were produced according to the procedure described in Nonpatent Reference 8.

Example 3

Figure 5A:
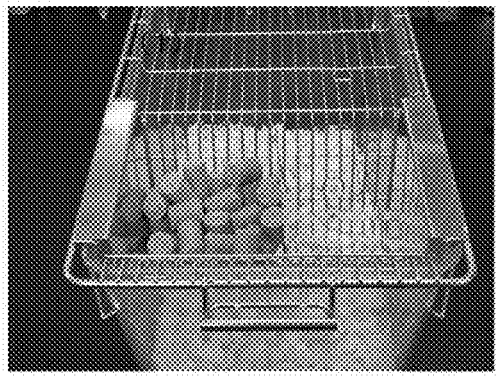
FIGS. 5A and 5B are photographs substituted for a drawing.
Figure 5B:
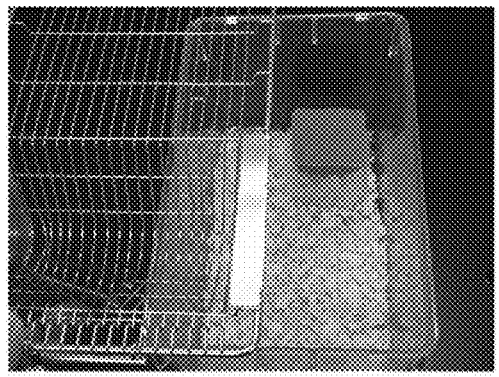

[Raising Girdin Knockout Mice]
In Example 1, the feed were switched from the solid feed (manufactured by Japan CLEA, CLEA Rodent Diet CE-2) that had been given up to that point to a soft feed (jelly-like feed) of the following formulation on day 8 postpartum. The Girdin knockout mice also continued to be given the same soft feed after weaning.
  Powdered agar (Morita Shoten, model no. 73017): 234 g
  Powdered feed (Japan CLEA, CLEA Rodent Diet CA-1): 2754 g
  Tap water: 18 L FIG. 5A is a photograph showing the feeding method before switching the feed. Solid feed was placed on the outside of the rearing cage. FIG. 5B is a photograph showing the feeding method after switching the feed. Soft feed was placed in a plastic dish on top of the shavings inside the rearing cage.

Figure 6A:
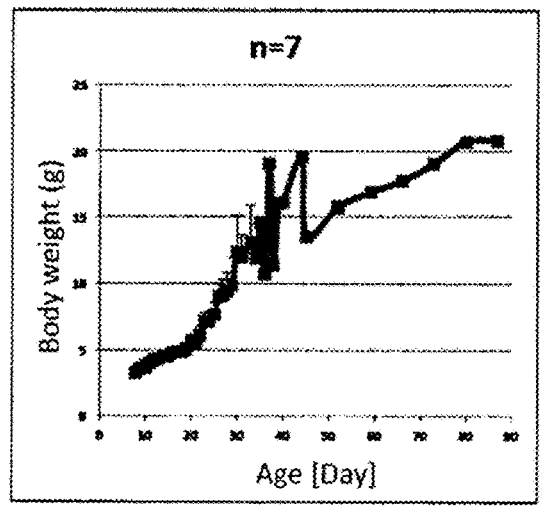
FIG. 6A is a graph showing the weight curve of the Girdin knockout mice raised in Example 2.
Figure 6B:
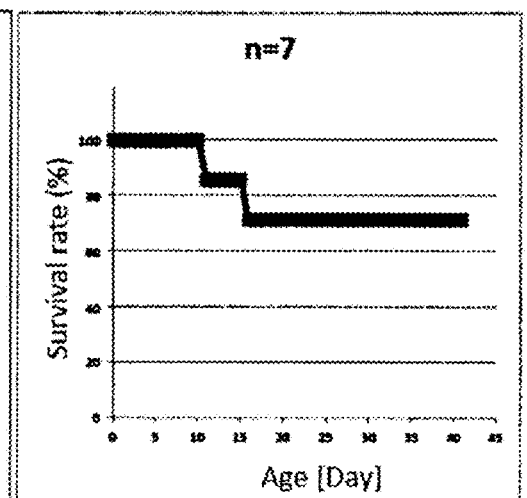
FIG. 6B is a graph showing the survival rate.

FIG. 6A is a graph showing the weight curve of the Girdin knockout mice raised in Example 3. The body weight of the mice increased smoothly with time. FIG. 6B is a graph showing the survival rate. Although one mouse died on day 12 and another on day 16, the other mice grew into adults.

Figure 7:
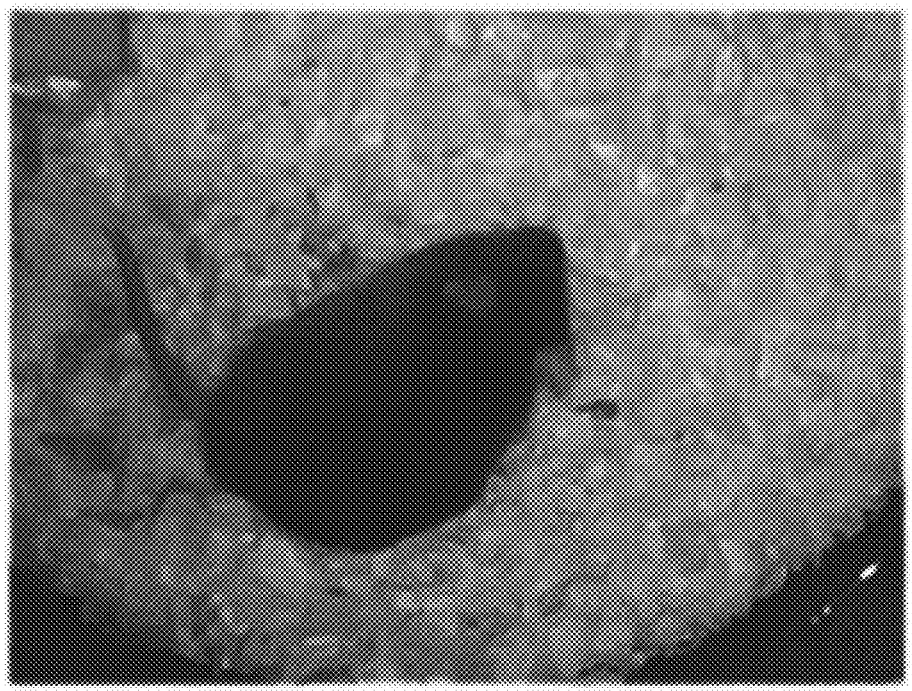
FIG. 7 is a photograph substituted for a drawing and is a photograph of a 280-day-old Girdin knockout mouse raised in Example 2.

Furthermore, Girdin knockout mice raised separately by the same method as in Example 3 are surviving at the age of 130 days as of today, Sep. 30, 2014. Other Girdin knockout mice raised by the same method lived healthily to the age of 382 days and 353 days, respectively, when they were sacrificed for experimentation. FIG. 7 is a photograph of a Girdin knockout mouse raised by the same method as in Example 3 at the age of 280 days.

Comparative Example 1

Figure 8:
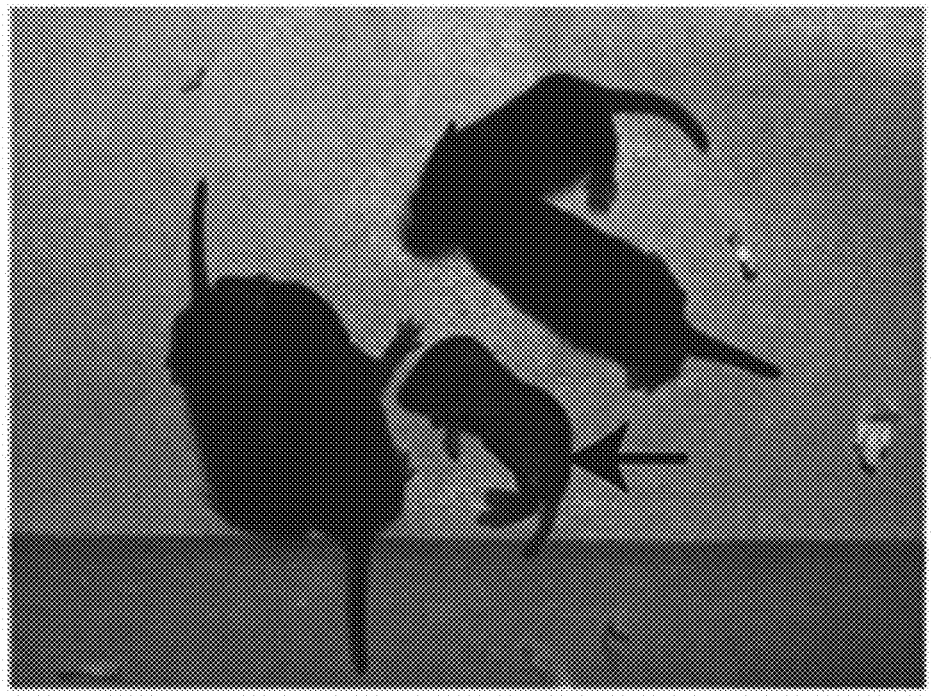
FIG. 8 is a photograph substituted for a drawing and is a photograph of littermates of a Girdin knockout mouse (arrow) that died at the age of eight days raised by the method of Comparative Example 1.

Girdin knockout mice were raised in the same way as in Example 3 using the mice of Example 2 except that the mother mice continued to be given solid feed without switching the feed after delivery. FIG. 8 is a photograph of 8-day-old mice raised by the method of Comparative Example 1. As shown in the photograph, the littermates survived without incident, but the Girdin mouse shown by the arrow was extremely small and was confirmed to be dead. The other Girdin knockout mice also gained virtually no weight from around 10 days after birth, and the death of all of them was confirmed by day 29, as shown in FIG. 2.

Example 4

The following combination of feed was used instead of the feed in Example 3. Knockout mice were raised by the same procedure as in Example 3 except that mice of almost pure C57 BL/6 genetic background backcrossed with the mice of Example 1 were used instead of the mice of Example 1 (mixed background of 129SV and C57 BL/6 which is the genetic background of ES cells).

(1) Agar feed: same as in Example 3.

(2) Milk jelly: Markan Co. strawberry milk jelly (http://www.yodobashi.com/markan-strawberry milk jelly/pd/100000001002322150/)

(3) Soaked feed: Produced by adding 20 g of water to 10 g of powdered feed (Japan CLEA, CLEA Rodent Diet CA-1) and kneading.

Figure 9:
FIG. 9 is a photograph substituted for a drawing and is a photograph of three types of feed in a cage.
Figure 10A:
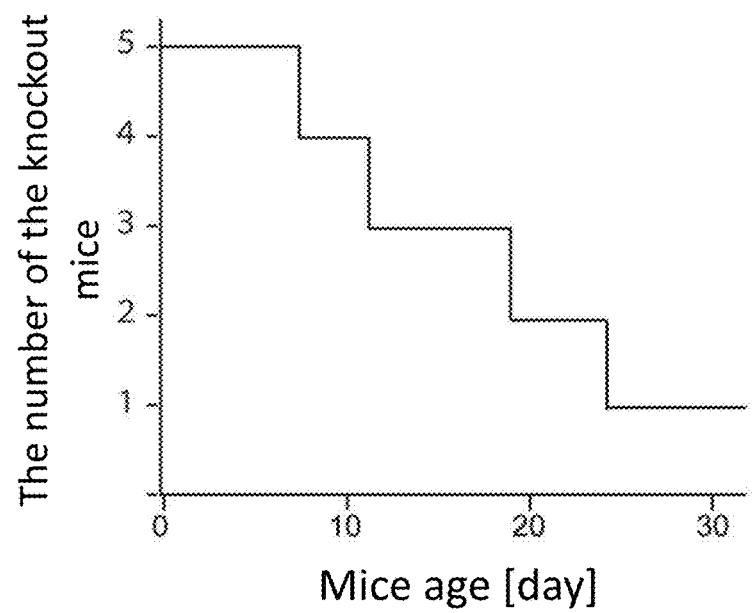
FIG. 10A is a graph showing the survival rate of the mice of Example 4.
Figure 10B:
FIG. 10B is a photograph substituted for a drawing and is a photograph of a Girdin knockout mouse of Example 4 at the age of 43 days.

FIG. 9 is a photograph of the three types of feed within the cage. FIG. 10A is a graph showing the survival rate of the mice of Example 4. Of five mice, one grew to an adult. FIG. 10B is a photograph of a Girdin knockout mouse at the age of 43 days. Furthermore, as was mentioned above, the mice of Example 1 and also Example 2 were of mixed background, but the mice of Example 4 were of backcrossed almost pure C57 BL/6 background. It is known that the majority of knockout mice of mixed background can be weaned, but the survival rate of those of C57 BL/6 background is low. However, in Example 4, surprisingly enough, long-term raising of a knockout mouse of C57BL/6 background was successful. This individual is 222 days old and weighs 20.5 g as of today, Oct. 9, 2015.

Since the above results clarify that adult Girdin knockout mice are obtained by devising a feeding method, Girdin knockout mice can be used in various experiments in addition to the experimental goals described in Nonpatent Documents 7 and 8.

In addition, the symptoms of MTLE were studied in greater detail below since the Girdin knockout mice presented symptoms of MTLE during the course of rearing.

Example 5

[Construction of a Video Monitoring System for Screening a Substance for Suppressing MTLE and Selecting a Technique for Suppressing MTLE, and a Screening Method and selection Method]

Figure 11:
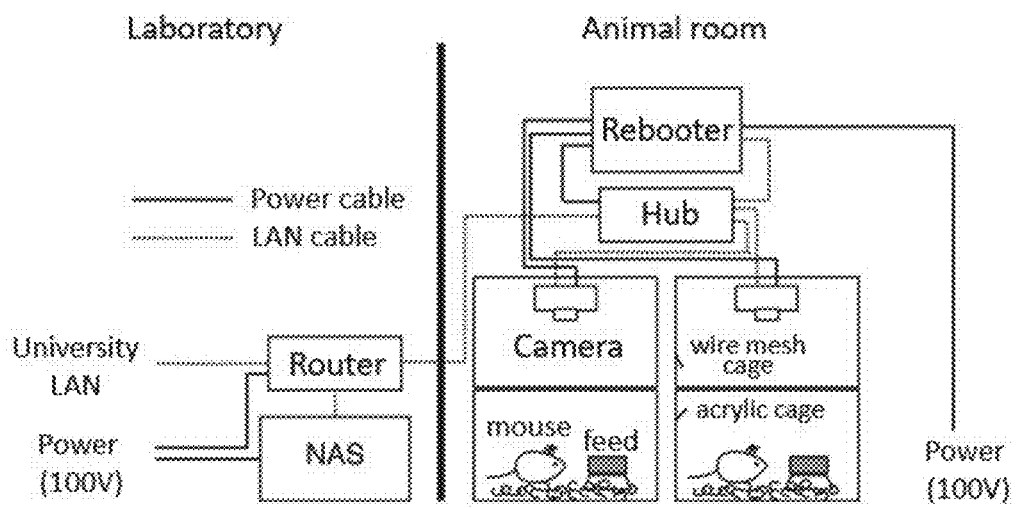
FIG. 11 is a drawing showing the outline of a video observation system produced in Example 5.

Next, a video observation system was constructed to screen substances for suppressing MTLE and to select techniques for suppressing MTLE using the Girdin knockout mice of the present invention. FIG. 11 is a drawing showing the outline of a video observation system produced in Example 5.

Specifically, an imaging device was constructed by combining two network cameras (I-O Data Co., model no. TS-WLC2 and model no. TS-WPTCAM), an NAS (I-O Data Co., model no. HDL-XR4.0), a router (I-O Data Co., LAN Gigabit router, model no. WN-AC1600DGR), a large-capacity HDD (Western Digital Co., WD My Book 4.0 TB, model no. WDBFJK0040HBK-SESN), and a hub (Elecom Co., gigabit switch Hub 5 port metal, white, model no. LAN-GSW05P). In addition, a rebooter (Meikyo Electric Co., Ltd., Watch Boot light, model no. RPC-M5C) was incorporated for remote rebooting in event of failure. The mice were placed in a mouse cage (Neuroscience Co., EEG/EMG measurement cage for mice, model no. 8228), covered by a wire mesh cage with good breathability, and the cameras were installed inside. The whole device was placed in an animal room, connected to the university network using a LAN cable, and image analysis and rebooting from a university laboratory or outside the university were enabled using a VPN (virtual private network). The Girdin knockout mice were placed on a lighting cycle of 12 hours on (9 a.m.-9 p.m.) and 12 hours off (9 p.m.-9 a.m.) at 25° C., which are normal rearing conditions for mice. Filming by the two cameras was controlled using software (QWATCH) on an I-O Data Co. browser, and both modes of continuous filming (manual file) and motion-detection filming (event file) that stores images only when the mouse moves were filmed in parallel. Motion detection was set at a sensitivity of 70% and threshold of 70. Filming was performed in night vision mode by 24-hour infrared beam to keep the motion detection sensitivity constant during lights on and off. All files were stored in the large-capacity HDD. Manual file analysis was performed using a laptop (Apple, MacBook Pro 15-inch, Mid 201, processor 2.8 GHz Intel Core i7, Mac OSX Lion 10.7.5). Scenes of grand mal seizures were trimmed, including several tens of seconds before and after, using the image software QuickTime Player 7 (Apple, for OSX), stored separately, and the seizure time was compiled into a list. The event files were analyzed using a Video LAN Association freeware VLC media player (Version 2.1.4 Rincewind Intel 64 bit).

Figure 12:
FIG. 12 is a photograph substituted for a drawing and is an image clipped from moving image data at the moment of a grand mal seizure.

Girdin knockout mice of Examples 1 and 2 were raised to the age of 33-29 days by the procedure of Example 3. A total of 14 mice, eight Girdin knockout mice with a modified exon 2 of Example 1 and six Girdin knockout mice with a modified exon 3 of Example 2, were placed separately in mouse cages of the video monitoring system produced in Example 4. The cameras were run constantly, and the mice were observed for approximately half a year. During that approximately half a year, a total of 873 grand mal seizures were filmed and recorded in all of the mice, and various incidental conditions associated with the grand mal seizures (many occurred during lights on, some developed during sleep, seizures were rare while eating feed, etc.) were discovered. FIG. 12 is a representative image clipped from moving image data at the moment of a grand mal seizure. We also succeeded in filming a "status epilepticus death" in which a mouse that had been healthy and eating feed steadily until just before death died at the end of a grand mal seizure that lasted close to ten minutes.

As was mentioned above, 100% of the Girdin knockout mice of Example 1 and Example 2 present symptoms of MTLE and can therefore be used in screening a substance for suppressing MTLE and selecting a technique for suppressing MTLE. In screening a substance for suppressing MTLE, for example, a candidate substance may be included in the feed, and a judgement made as to whether or not it suppresses the frequency and/or severity of seizures by using the video observation system produced in Example 4. In selecting a technique for suppressing MTLE, a judgement may be made as to whether or not the frequency and/or severity of seizures is suppressed by using the video observation system after performing an epileptic seizure treatment such as vagus nerve stimulation (VNS), performing massage, fitting with a corset or a soundwave or vibration stimulation generator, or performing a therapy related to lifestyle (adjustment of diet and/or type of diet, exercise, etc.).

Example 6

[Confirmation of Conditions Required of an MTLE Animal Model]

Since it was evident from the video observation of Example 5 that the Girdin knockout mice of the present invention develop MTLE, analysis of the brain tissue was conducted. Girdin knockout mice of Examples 1 and 2 that were several months old and had been raised by the method described in Example 3 were used in analysis conducted by the following procedure.

<Staining of Brain Tissue>

Figures 13A, 13B:
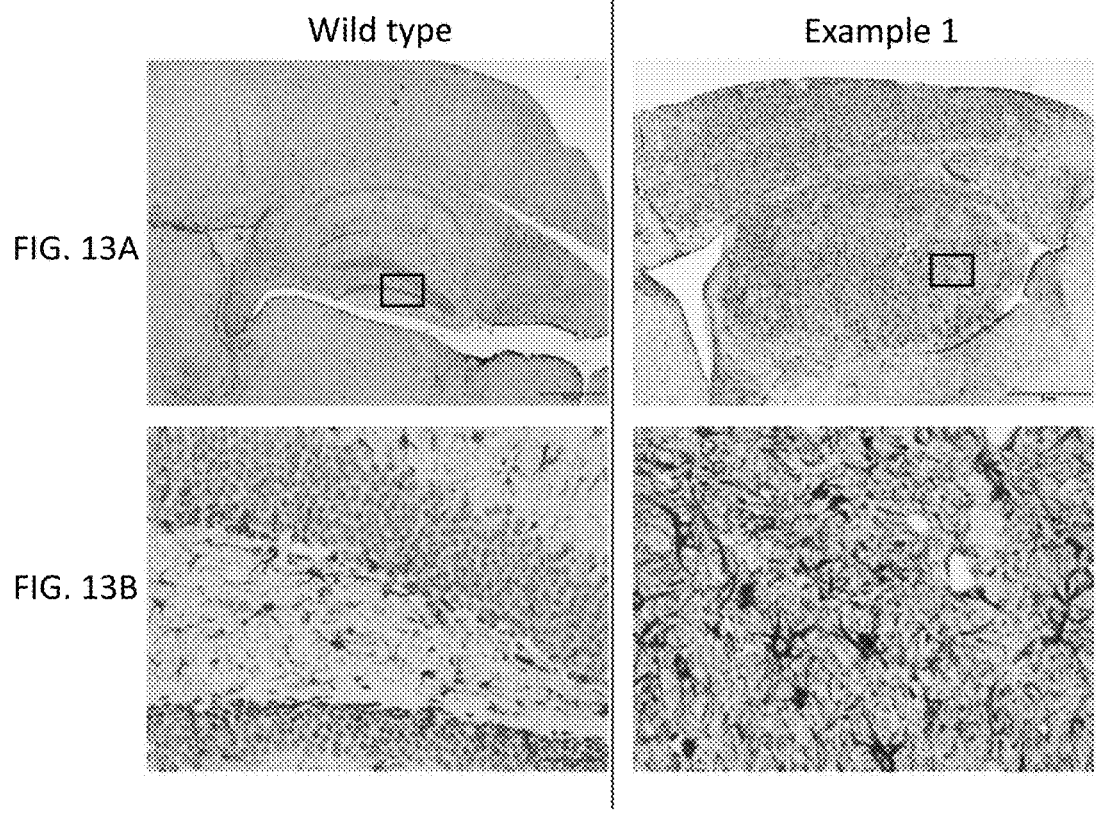
FIGS. 13A and 13B are photographs substituted for a drawing.

The adult mouse brain was removed, and paraffin sections prepared by the usual method were stained by anti-GFAP antibody, and the nuclei were stained by hematoxylin. As a control, wild type mice were also stained by the same procedure. FIG. 13A is photographs of stained sagittal sections of the brains of Example 1 and wild type mice. FIG. 13B is enlarged photographs of the parts surrounded by square of FIG. 13A. FIG. 14A is photographs of stained coronal sections of the brains of Example 2 and wild type mice by the same procedure. FIG. 14B is enlarged photographs of the parts surrounded by square of FIG.14A.

In the photographs shown in FIGS. 13A, 13B, 14A and 14B, the brown signal indicates astrocytes stained by GFAP. The brown signal was concentrated in the hippocampus, and the hippocampus was hypertrophic in both types of adult Girdin knockout mice of Examples 1 and 2. In addition, based on the enlarged photographs of FIGS. 13B and 14B, enormous astrocytes with enlarged protrusions, which are not seen in the wild type, were seen in the mice of Examples 1 and 2. This indicates hippocampal sclerosis. In addition, no hippocampal sclerosis could be found other than in the cerebral cortex and amygdala adjacent to the hippocampus as a result of examining the photographs.

<EEG Measurement>

Figure 16A:
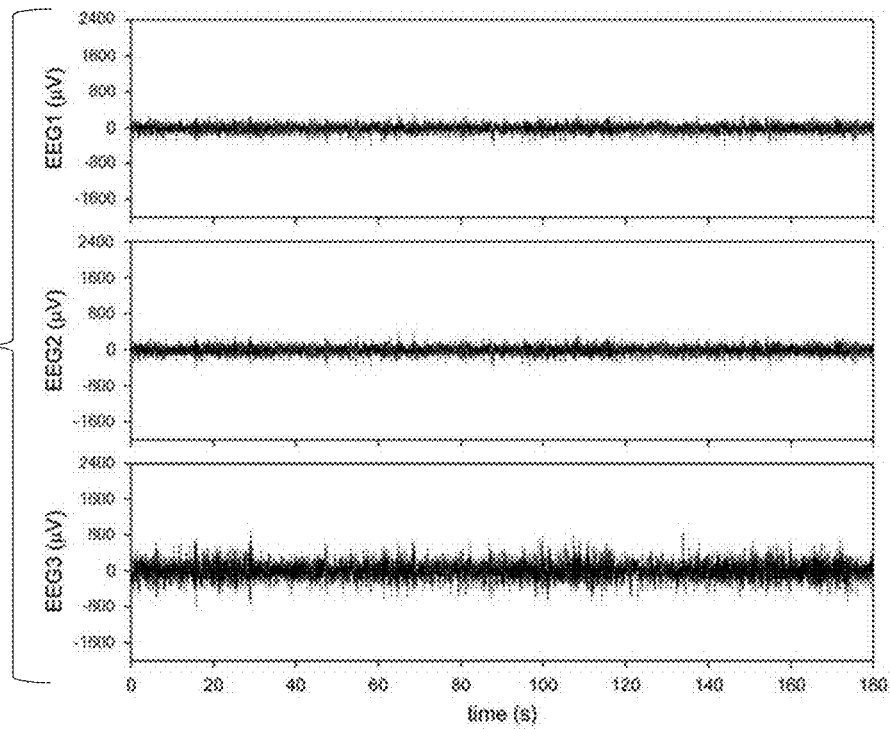
FIG. 16A shows the EEG at rest of a wild type.
Figure 16B:
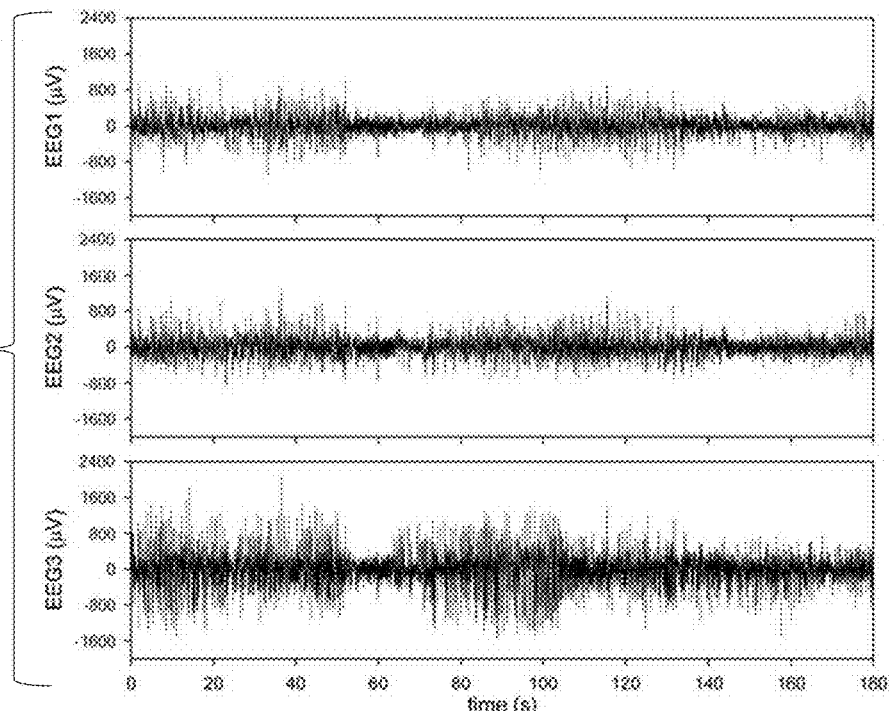
FIG. 16B shows the EEG at rest of a mouse of Example 2.

The EEG was measured in a state in which the scalp of the parietal region of an adult mouse brain of Example 2 was removed and electrodes were embedded in the skull and fixed by resin. FIG. 15 shows the positions of the electrodes (EEG1, EEG2, EEG3) embedded. FIG. 16A shows the EEG at rest of a wild type. FIG. 16B shows the EEG at rest of a mouse of Example 2. FIG. 16C shows the EEG of a mouse of Example 2 during a grand mal seizure. As a result, high-amplitude brain waves not seen in the wild type were observed continuously for 24 hours in all electrodes in mice of Example 2, and the electrode directly above the hippocampus (EEG3) in particular indicated the highest amplitude. Brain waves (bursts) of higher amplitude and higher frequency than the background were observed in synchronization with grand mal seizures from this EEG3. Considering that the lesions centering on the hippocampus were always seen in the histopathology, it can be assumed that the grand mal seizures are seizures originating from the hippocampus that have become generalized.

As is evident from <Staining of brain tissue> and <EEG measurement> above, the Girdin knockout mice of the present invention could be confirmed to fulfill the conditions required by Felix Rosenow et al.:

(1) hippocampal sclerosis should be present,
(2) extrahippocampal brain damage should be limited, and
(3) spontaneous epilepsy that can be said to be of hippocampal origin should be present.

Although Girdin knockout mice themselves were known in the past, this is the first time that it has been clarified that Girdin knockout mice have the phenotype required of an MTLE animal model based on the video observations of Example 5 and the brain tissue analysis and EEG measurements of Example 6. One hundred percent of the Girdin knockout mice of the present invention were clarified to develop MTLE. Therefore, the Girdin knockout mice produced in the present invention were confirmed to be highly useful in the screening of substances for suppressing MTLE and the selection of techniques for suppressing MTLE. In addition, since devising a feeding method makes it possible to obtain Girdin knockout mice 30 or more days of age that did not exist in the prior art, as shown in Example 3 and Comparative Example 1, the mice can be used in various animal experiments in addition to the screening of substances for suppressing MTLE and the selection of techniques for suppressing MTLE.

INDUSTRIAL APPLICABILITY

The Girdin knockout mouse of the present invention fulfills all of the conditions [(1) hippocampal sclerosis should be present,(2) extrahippocampal brain damage should be limited, and (3) spontaneous epilepsy that can be said to be of hippocampal origin should be present] required of an animal for screening a substance for suppressing MTLE and selecting a technique for suppressing MTLE, and can be raised to an adult of 30 or more days of age.

It is therefore useful in the development of MTLE therapeutic drugs and therapeutic methods in universities, medical facilities, pharmaceutical companies, and the like since it can be used in experiments using adult animals in addition to the screening of substances for suppressing MTLE and the selection of techniques for suppressing MTLE.

What is claimed is:

1. A homozygous knockout mouse 30 or more days of age, whose genome comprises a knocked out endogenous Girdin gene that results in lost function of the Girdin gene, wherein the knockout mouse exhibits the phenotypes of (1), (2), and (3) below:
   (1) hippocampal sclerosis is present,
   (2) extrahippocampal brain damage is limited, and
   (3) spontaneous epilepsy that can be said to be of hippocampal origin is present.

2. The knockout mouse according to claim 1, wherein the knockout mouse is raised on soft feed.

3. The knockout mouse according to claim 2, wherein the soft feed is jelly-like.

* * * * *